(12) United States Patent
Kim et al.

(10) Patent No.: US 6,829,328 B2
(45) Date of Patent: Dec. 7, 2004

(54) METHOD FOR MAKING QUANTITATIVE ANALYSIS OF NICKEL

(75) Inventors: Binn Kim, Seoul (KR); Hyun Ja Kwon, Kyonggi-do (KR); Kyu Ho Park, Kyonggi-do (KR)

(73) Assignee: LG. Philips LCD Co., Ltd., Seoul (KR)

(*) Notice: Subject to any disclaimer, the term of this patent is extended or adjusted under 35 U.S.C. 154(b) by 195 days.

(21) Appl. No.: 10/309,279

(22) Filed: Dec. 4, 2002

(65) Prior Publication Data

US 2003/0123607 A1 Jul. 3, 2003

(30) Foreign Application Priority Data

Dec. 29, 2001 (KR) ...................................... P2001-88450

(51) Int. Cl.⁷ ................................................. G01T 1/36
(52) U.S. Cl. .............................. 378/44; 378/45; 378/50; 438/14; 438/486
(58) Field of Search .............................. 378/44, 45, 46, 378/50; 438/14, 478, 486, 584

(56) References Cited

U.S. PATENT DOCUMENTS 5,754,620 A  *  5/1998  Hossain et al. ............... 378/45

* cited by examiner

*Primary Examiner*—Edward J. Glick
*Assistant Examiner*—Courtney Thomas
(74) *Attorney, Agent, or Firm*—Morgan, Lewis & Bockius LLP

(57) ABSTRACT

A method for making a quantitative analysis of nickel that includes the steps of providing an amorphous silicon layer, forming an insulating film on the amorphous silicon layer, depositing nickel on the insulating film, etching a defined portion of the nickel with an etchant to create a specimen, drying the specimen on an AP1 film and subjecting the dried specimen to energy dispersive X-ray fluorescence analysis.

20 Claims, 12 Drawing Sheets

| Sample No | Power (W) | ED-XRF | | TOF-SIMS |
|---|---|---|---|---|
| | | Ni/API film | Ni/Si/SiO$_2$/Glass | Ni/Si/SiO$_2$/Glass |
| #1 | 100 | - | $3.94 \times 10^{13}$ | $2.12 \times 10^{13}$ |
| #2 | 150 | - | $9.92 \times 10^{13}$ | $6.39 \times 10^{13}$ |
| #3 | 250 | $2.47 \times 10^{14}$ | $2.04 \times 10^{14}$ | $1.55 \times 10^{14}$ | atoms/cm$^2$

METHOD FOR MAKING QUANTITATIVE ANALYSIS OF NICKEL

This application claims the benefit of the Korean Application No. P2001-88450 filed in Korea on Dec. 29, 2001, which is hereby incorporated by reference in its entirety.

BACKGROUND OF THE INVENTION

1. Field of the Invention

The present invention relates to a method for making a quantitative analysis of nickel, and more particularly, to a method for making a quantitative analysis of nickel to determine an amount of nickel required for converting amorphous silicon into polycrystalline silicon by MIC (Metal Induced Crystallization).

2. Description of the Related Art

Due to features of the Liquid Crystal Display (LCD), such as a low driving voltage, a low power consumption, full-color realization, light weight, compactness, and the like, application of the LCD varies widely. For example, devices, such as watches, calculators, monitors for PCs, and notebook computers, TVs, instrument panel for an airplane, PDA (Personal Digital Assistants) and mobile stations use an LCD. Typically, an LCD includes a liquid crystal display panel part for displaying a picture, and a circuit part for driving the liquid crystal display panel. The liquid crystal display panel part has a first substrate having thin film transistor (TFT) array formed thereon, a second substrate having color filter array formed thereon, and a liquid crystal layer formed between the two substrates.

The first substrate of the LCD, having the TFT array formed thereon, has a plurality of gatelines arranged in one direction at fixed intervals and a plurality of datalines arranged in a direction perpendicular to the gatelines at fixed intervals. Pixel regions are defined between the gatelines and the datalines. A pixel electrode is formed in each pixel region. A plurality of thin film transistors are formed in the pixel regions adjacent to where the gatelines and the datalines cross, respectively. The gate, source and drain of each thin film transistor are respectively connected to a gateline, dataline and a pixel electrode. Each thin film transistor is turned on/off in response to a driving signal from the gateline such that a picture signal is transmitted from the dataline to the pixel electrode.

The second substrate of the LCD, having the color filter array formed thereon, has a black matrix layer for shielding light from parts of the pixel regions. A RGB color filter layer is formed opposite to the pixel regions for displaying colors. A common electrode is formed on the entire surface of the second substrate, including the color filter layer. In an alternative, the common electrode may be formed on the first substrate in an In Plane Switching (IPS) mode LCD.

The foregoing first and second substrates are bonded together such that a gap is maintained between the two substrates. In the alternative, spacers can be positioned between the substrates to assist in maintaining a uniform gap across the LCD. A liquid crystal layer is positioned in the gap between the two substrates.

In order for an LCD to have high definition and high resolution, especially for moving images, a high speed or highly responsive thin film transistor is required. A high speed thin film transistor requires a high degree of electrophoresis in the active layer of the thin film transistor. Thus, a polycrystalline silicon layer, rather than an amorphous layer, is used to increased the degree of electrophoresis in the active layer. Further, the use of the polycrystalline silicon as an active layer enables cost reduction of a driving Integrated Circuit (IC) by forming the driving IC on the first substrate having the TFT array formed thereon, which facilitates easy fitting since the driving IC is not on a separate substrate. Furthermore, using polycrystalline silicon reduces power consumption since polycrystalline silicon has less resistance than amorphous silicon.

The polycrystalline silicon cannot be deposited directly on the glass substrate of the LCD because of the high temperature for such a polycrystalline deposition. However, amorphous silicon can be deposited on the glass substrate. Then, the amorphous silicon is crystallized into polycrystalline silicon.

The amorphous silicon may be crystallized into polycrystalline silicon by either a solid state crystallizing method or a Continuous Grain Silicon (CGS) method. In the solid state crystallization method, amorphous silicon is deposited on the substrate. The amorphous silicon is then crystallized by using a heat treatment of about 20 hours at 600° C. under a vacuum. In the CGS method, amorphous silicon is deposited on the glass substrate, the part in which a channel region of the thin film transistor is to be formed therein is masked off by a silicon oxide film, or the like. Then a Ni layer is deposited on the amorphous silicon such that Ni is not deposited on the channel part and the thickness of Ni on the source/drain regions of the thin film transistor is greater than a few tens of Å. Subsequently, the amorphous silicon is crystallized into polycrystalline silicon. The source and drain regions crystallize due to the Ni on their surfaces and the channel region crystallizes towards its center from the crystallized source and drain regions. The semiconductive properties of the source and drain regions have been diminished because of the large presence of Ni while the channel region is only slightly effected by trace amounts of Ni that may have migrated from the source and drain regions.

Typically, nickel is used when amorphous silicon is crystallized using a metal. Nickel improves speed and completeness of the crystallization of amorphous silicon into polycrystalline silicon. However, too much nickel undermines the semiconductive properties of the subsequently formed polycrystalline silicon. Accordingly, crystallizing amorphous silicon using a nickel needs a method for accurately measuring and/or determining quantity of nickel deposited on amorphous silicon.

A related art method for making quantitative analysis of nickel will be explained, with reference to the attached drawing. FIG. 1 explains a related art method for making a quantitative analysis of nickel. Measuring a thickness of deposited nickel is effective in making a quantitative analysis of nickel. Physical properties of a surface and a thickness of a thin film can be detected by using an ellipsometer. As shown in FIG. 1, an ellipsometer includes a light source 102, a polarizing prism 103 for linearly polarizing light from the light source, a quarter wave compensator 104 for elliptically polarizing the linearly polarized light, an analyzer 105 for analyzing a light that is reflected from and refracted at a specimen 101, and a light detector 106 for detecting the light through the analyzer 105.

A related art method for measuring a thickness of a thin film by using the ellipsometer will be explained in reference to FIG. 1. The polarizing prism 103 and the quarter wave compensator 104 are rotated such that light is having elliptically polarized by the polarizing prism 103 and the quarter wave compensator 104. The elliptically polarized light is incident to a surface of a specimen 101, reflected, and refracted at the specimen 101, is linearly polarized.

Eventually, a thickness of the specimen can be measured by an equation which describes optical characteristics of the specimen 101 and is derived from optical parameters by using rotation angles of the polarizing prism 103, the quarter wave compensator 104, and the analyzer 105. The thickness can be measured to a few thousands of Å. Thus, a thickness of nickel sputtered on amorphous silicon can be measured by using the ellipsometer.

However, the foregoing related art method for making a quantitative analysis of nickel by a thickness measurement using an ellipsometer has the following problems. First, measurement of the thickness is complicated since the thickness is measured by using a polarized light incident to a specimen. Second, the analysis costs are high because of the equipment used to measure thickness with polarized light incident to the specimen. Third, a thickness below 1 Å can not be measured with an ellipsometer.

SUMMARY OF THE INVENTION

Accordingly, the present invention is directed to a method for making quantitative analysis of nickel that substantially obviates one or more of the problems due to limitations and disadvantages of the related art.

An object of the present invention is to provide a method for making a quantitative analysis of nickel for crystallizing amorphous silicon in which a solution of a portion of nickel deposited on amorphous silicon is etched by an etchant and subjected to an Energy Dispersive X-ray Fluorescence (ED-XRF) analysis to determine a thickness of the nickel resulting from the deposition process of the nickel.

Another object of the present invention is to provide a method for making a quantitative analysis of nickel for crystallizing amorphous silicon in which an amount of nickel is deposited on an AP1 film and is subjected to an ED-XRF analysis to determine a thickness the of nickel resulting from the deposition process of the nickel.

Another object of the present invention is to crystallize amorphous silicon with nickel deposited on the amorphous silicon in which process parameters of the deposition process are determined from a quantitative analysis of nickel using an ED-XRF analysis.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the present invention, as embodied and broadly described, a method for making a quantitative analysis of nickel includes the steps of providing an amorphous silicon layer, forming an insulating film on the amorphous silicon layer, depositing nickel on the insulating film, etching a defined portion of the nickel with an etchant to create a specimen, drying the specimen on an AP1 film and subjecting the dried specimen to energy dispersive X-ray fluorescence analysis.

In another aspect of the present invention, there is provided a method for making quantitative analysis of nickel that includes the steps of providing a substrate, placing an AP1 film having a predetermined area on the substrate, depositing nickel on the AP1 film, peeling the AP1 off of the substrate and subjecting the peeled AP1 film to energy dispersive X-ray fluorescence analysis.

In another aspect of the present invention, there is provided a method for crystallizing amorphous silicon that includes depositing nickel under different depositing conditions, etching a predetermined area of nickel in each deposition with etchant to prepare specimens for each of the depositing conditions, drying the specimens on AP1 film, subjecting the specimens to energy dispersive X-ray fluorescence analysis, determining an optimal nickel depositing condition according to results of the energy dispersive X-ray fluorescence analyses on the specimens, depositing nickel on amorphous silicon with the optimal depositing condition and crystallizing the amorphous silicon into polycrystalline silicon.

In another aspect of the present invention, there is provided a method for crystallizing amorphous silicon that includes providing substrates, placing an AP1 film having a predetermined area on each of the substrates, depositing nickel on the AP1 film on each substrate such that there are depositions of nickel under different depositing conditions, peeling the AP1 film off of the substrates, subjecting the nickel deposited AP1 film to energy dispersive X-ray fluorescence analysis, determining an optimal nickel depositing condition according to results of the energy dispersive X-ray fluorescence analyses on the specimens, depositing nickel on amorphous silicon with the optimal depositing condition and crystallizing the amorphous silicon into polycrystalline silicon.

It is to be understood that both the foregoing general description and the following detailed description are exemplary and explanatory, and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

DETAILED DESCRIPTION OF THE PREFERRED EMBODIMENT

Reference will now be made in detail to the preferred embodiments of the present invention, examples of which are illustrated in the accompanying drawings.

Amorphous silicon may be crystallized by an Metal Induced Crystallization (MIC) method in which a minute amount of metal is deposited on amorphous silicon and heat treated. In the MIC method, the amorphous silicon with the minute amount of metal is subjected to heat treatment at 500~600° C. for approximately 10 hours to crystallize the amorphous silicon. To speed up the crystallization process, an electric field can be used. For example, amorphous silicon may be crystallized by a Field Enhanced Metal Induced Crystallization (FEMIC) method in which a minute amount of metal is deposited on amorphous silicon and an electric field is applied to the amorphous silicon together with a heat treatment at a temperature below 550° C. for about 30 minutes to achieve crystallization. In both the MIC and FEMIC methods, amorphous silicon is deposited on a substrate, a metal, such as nickel, is sputtered on the amorphous silicon to a thickness of less than 1 Å. Typically, nickel having a thickness below 1 Å is used as the metal in both the MIC and FEMIC methods. However, quantitative analysis of nickel can not be measured by an ellipsometer for a thickness below 1 Å.

Figure 1:
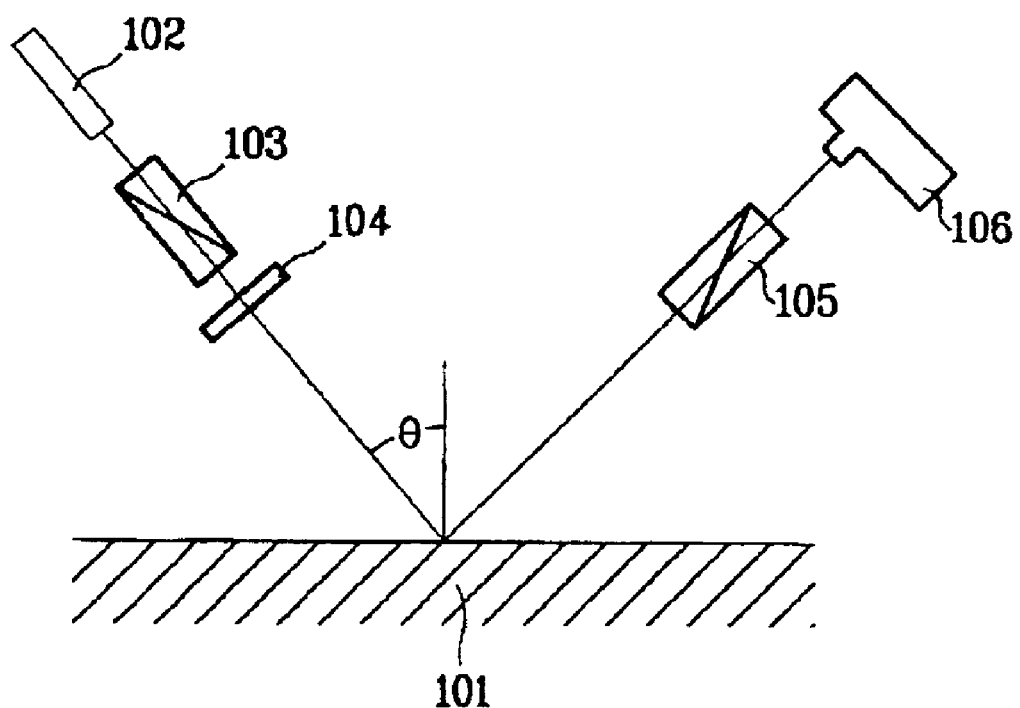
FIG. 1 explains a related art method for making a quantitative analysis of nickel.
Figure 2A:
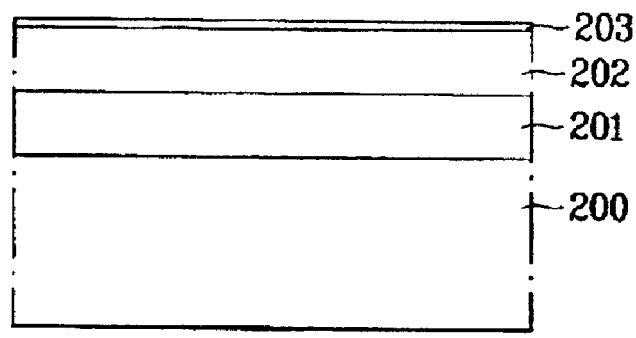
FIGS. 2A to 2E illustrate the steps of a method for making a quantitative analysis of nickel in accordance with a first preferred embodiment of the present invention.

FIGS. 2A to 2E illustrate the steps of a method for making a quantitative analysis of nickel in accordance with a first preferred embodiment of the present invention, wherein FIG. 2A illustrates a cross-sectional view, and FIGS. 2B through 2E illustrate plan views.

Referring to FIG. 2A, a buffer layer of $SiO_2$ or $SiN_x$ 201 is formed on a 350 mm×300 mm substrate 200. A layer of amorphous silicon a-Si:H 202 is formed on the buffer layer 201. A nickel layer 203 is sputtered thereon to a thickness of less than 1 Å. A natural oxide film, such as $SiO_2$, is allowed to formed on a surface of the amorphous silicon 202. In the alternative, an $SiO_2$ film can be formed by another oxidation method, such as steam oxidation.

Figure 2B:
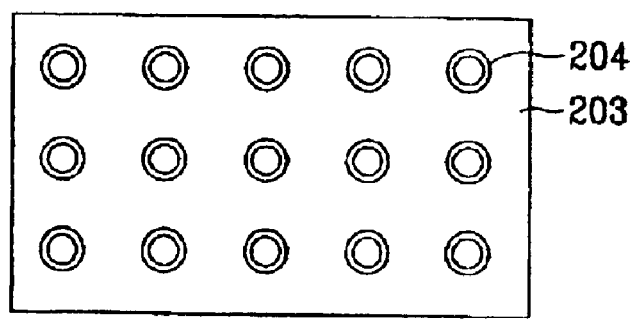

Referring to FIG. 2B, photoresist is applied to a photoresist applicator (not shown), and the photoresist applicator is stamped to form donuts of photoresist 204. The donuts of photoresist 204 are applied to the nickel layer 203 from the photoresist applicator (not shown). The substrate including the donuts of photoresist 204 is placed on a hot plate having a temperature of approximately 110° C. to bake the donuts of photoresist 204. The area within the inside of the donuts of photoresist 204 is known.

Figure 2C:
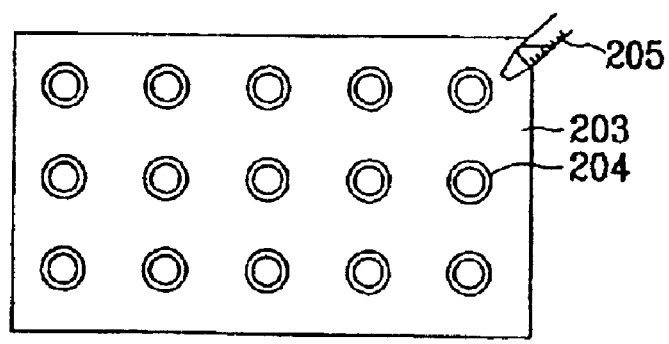

Referring to FIG. 2C, four or five drops of etchant 205 is dropped onto the nickel layer 203 inside each of the donuts of photoresist 204. The etchant 205 spreads out over the nickel layer within the insides of the donuts of photoresist 204. The inside of a donut of photoresist 204 defines an area that will be etched by the etchant. Experimental verification has shown that it is preferable to use a mixture of 5% HF:6% $H_2O_2$ as an etchant so that a subsequent ED-XRF analysis will be substantially accurate. Although etchants other than the mixture of 5% HF:6% $H_2O_2$ can be used, the 5% HF:6% $H_2O_2$ is preferable because it permits more accurate nickel quantity measurement as will be explained later in reference to FIG. 4.

Figure 2D:
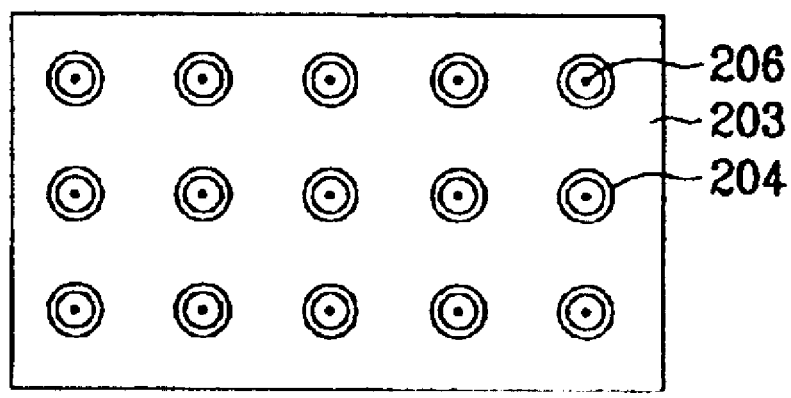

Referring to FIG. 2D, the etchant 205 etches the nickel, while also etching the naturally formed $SiO_2$ film that was formed on the amorphous silicon layer (not shown). The natural oxide and the nickel are dissolved by the etchant 205. A specimen 206, inclusive of the natural oxide film and the nickel, coheres into a big drop at a central part within the inside of the donuts of photoresist 204.

Figure 2E:
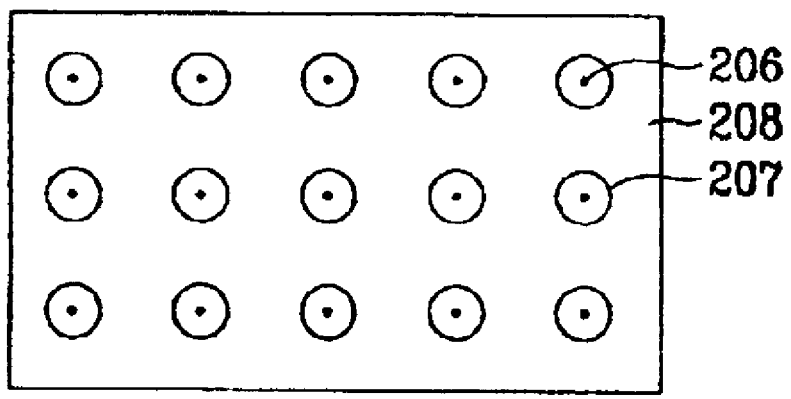

Referring to FIG. 2E, the specimen 206 is picked up with a micropipette and dropped on an AP1 film 207, which is on an AP1 film supporter 208. The specimen 206 is dried on a hot plate at a temperature of approximately 35~50° C. until all of the moisture and acid in the specimen are dried such that a nickel residue is left in the central part of the AP1 film 207 having a size of, for example, 2×2 mm. The AP1 film is formed of a plastic for analyzing small quantities of a specimen such that background peaks of the AP1 film in an Energy Dispersive X-ray Fluorescence (ED-XRF) analysis of the specimen are minimized. By using an ED-XRF analysis of the nickel specimen on the AP1 film, a measurement of a nickel peak together with the known area of the inside of the donut of photoresist can be used to obtain a concentration per a unit of area, such as $\mu g/cm^2$. Further, by taking specimens from across the substrate, distributive data for the nickel concentrations across the substrate can be determined.

Figure 3A:
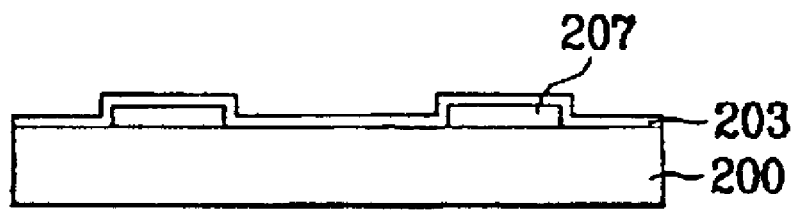
FIGS. 3A and 3B illustrate the steps of a method for making a quantitative analysis of nickel in accordance with a second preferred embodiment of the present invention.
Figure 3B:
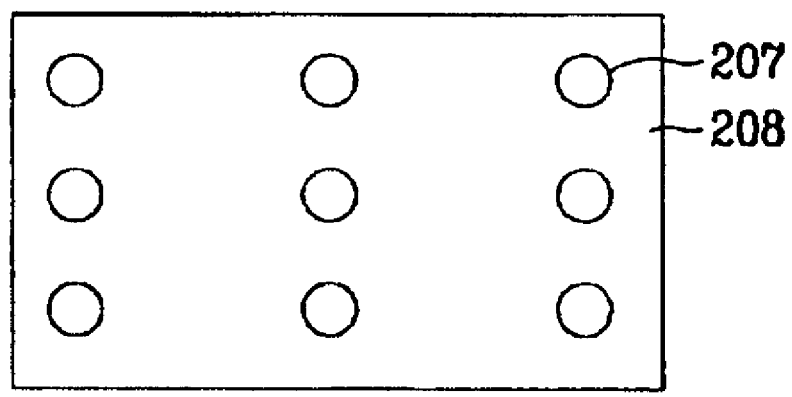

FIGS. 3A and 3B illustrate the steps of a method for making a quantitative analysis of nickel in accordance with a second preferred embodiment of the present invention, wherein FIG. 3A illustrates a cross-section, and FIG. 3B illustrates a plan view. Referring to FIG. 3A, AP1 films 207 having known dimensions are attached on a 350 mm ×300 mm sized substrate 200. Nickel 203 is sputtered across the entire surface of the substrate, including the AP1 films 207. Referring to FIG. 3B, the AP1 film 207 having nickel deposited thereon is peeled off from the substrate 200 and placed on a film supporter 208. The nickel on the AP1 film 207 is subjected to ED-XRF analysis. By using an ED-XRF analysis of the nickel specimen on the AP1 film, a measurement of a nickel peak together with the known dimensions of the AP1 film can be used to obtain a concentration per a unit of area, such as $\mu g/cm^2$.

Figure 4A:
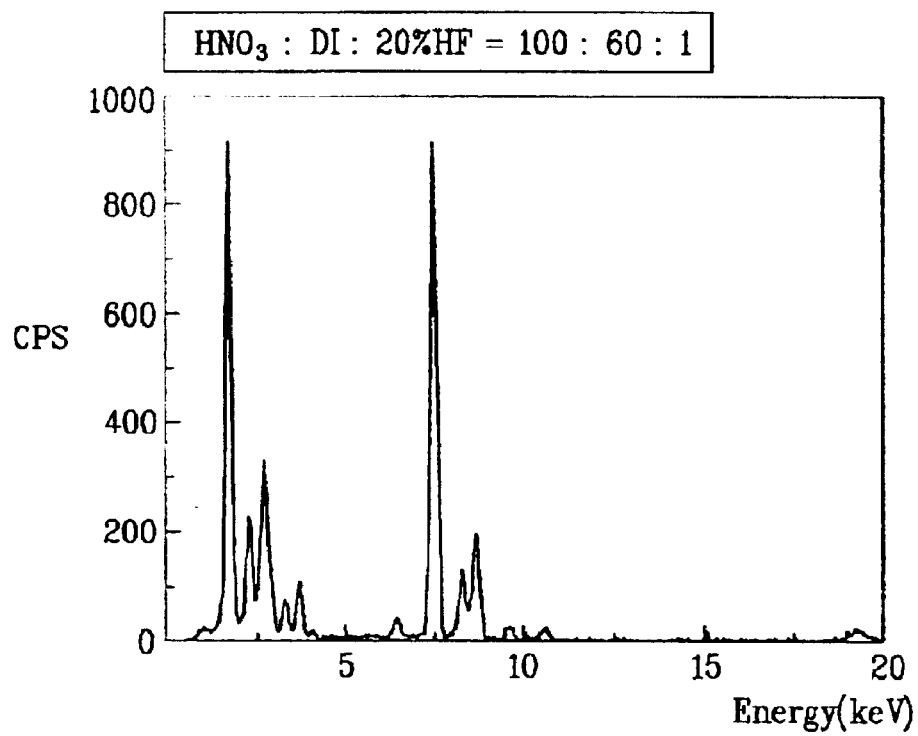
FIG. 4A illustrates a graph of an Energy Dispersive X-ray Fluorescence analysis of nickel etched by an etchant of a 100:60:1 mixture of $HNO_3$:DI:20% HF in accordance with a preferred embodiment of the present invention.
Figure 4B:
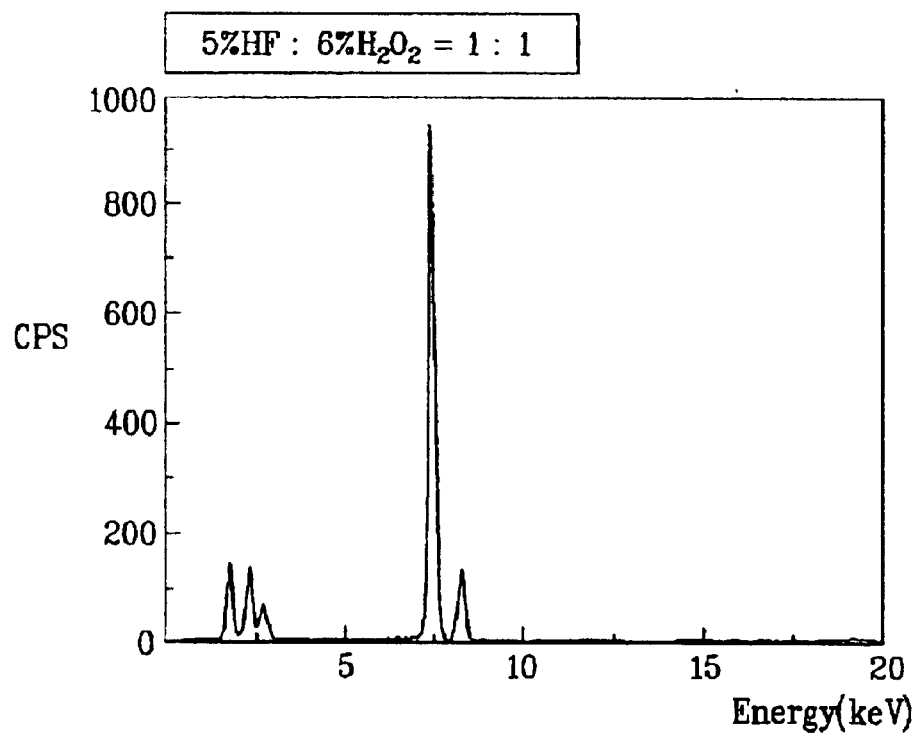
FIG. 4B illustrates a graph of an Energy Dispersive X-ray Fluorescence analysis of nickel etched by an etchant of a 1:1 mixture of 5% HF:6% $H_2O_2$ in accordance with a preferred embodiment of the present invention.

FIGS. 4A and 4B illustrate graphs of ED-XRF analyses for the nickel etchant in accordance with a preferred embodiment of the present invention, wherein FIG. 4A illustrates a graph of an ED-XRF analysis of a specimen etched by an etchant of a 100:60:1 mixture of $HNO_3$:DI:20% HF, and FIG. 4B illustrates a graph of an ED-XRF analysis of a specimen etched by an etchant of a 1:1 mixture of 5% HF:6% $H_2O_2$. Referring to FIG. 4A, when nickel is etched with a mixture of $HNO_3$:DI:20% HF in a ratio of 100:60:1, there is no single distinctive peak for only the nickel in the specimen (in the vicinity of 7.5 KeV) because the etchant etches not only the nickel, but also etches the natural oxide and the amorphous silicon. However, referring to FIG. 4B, when a specimen is etched with a mixture of 5% HF:6% $H_2O_2$ in a ratio of 1:1, there is only one distinctive peak for indicating the nickel composition of the nickel specimen because the etchant does not etch the amorphous silicon and the natural oxide. The efficiency of this nickel only etching is approximately 95%.

Figure 5:
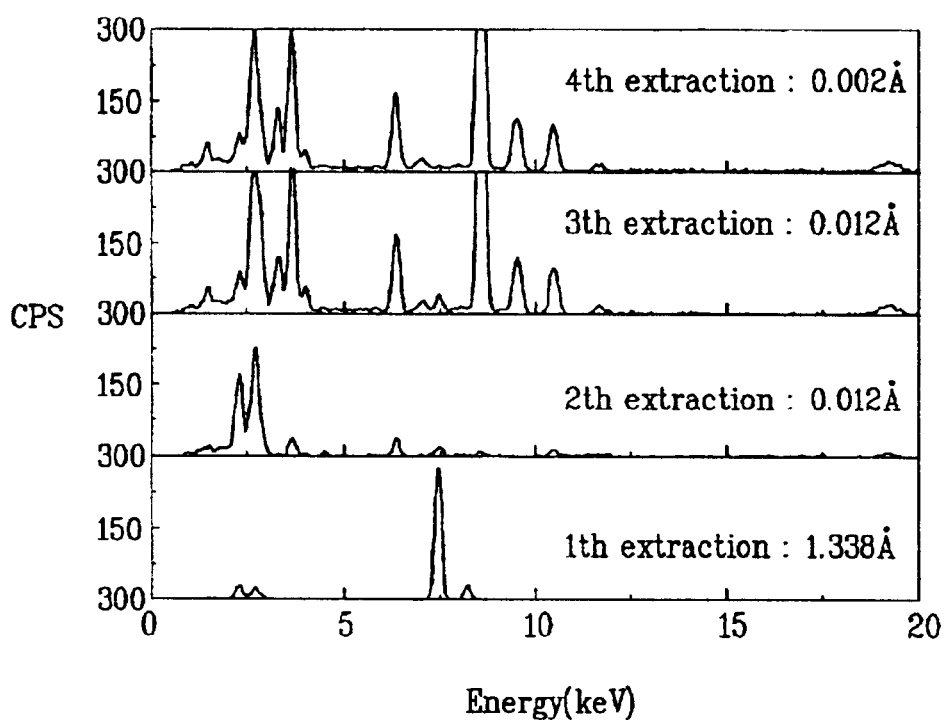
FIG. 5 illustrates Energy Dispersive X-ray Fluorescence analysis graphs of nickel etched and extracted a number of times in accordance with a preferred embodiment of the present invention.

FIG. 5 illustrates ED-XRF analysis graphs of etching and extracting nickel specimens twice from two different areas of a substrate. A nickel specimen is etched with etchant of the 1:1 mixture of 5% HF:6% $H_2O_2$, extracted, and subjected to ED-XRF analysis from a first area of a substrate for a first extraction. Then, a nickel specimen is etched with etchant of the 1:1 mixture of 5% HF:6% $H_2O_2$, extracted, and subjected to ED-XRF analysis from the same first area of the substrate for a second extraction. In addition, a nickel specimen is etched with etchant having the 100:60:1 mixture of $HNO_3$:DI:20% HF, extracted, and subjected to ED-XRF from a second area of a substrate for a third extraction. Subsequently, a nickel specimen is etched with etchant having the 100:60:1 mixture of $HNO_3$:DI:20% HF, extracted, and subjected to ED-XRF from the same second area of the substrate for a fourth extraction.

Referring to FIG. 5, when a nickel specimen is etched with an etchant having a 1:1 mixture of 5% HF:6% $H_2O_2$, almost all of the nickel is extracted, as shown in the first extraction and second extraction of the same area. Accordingly, an accurate quantitative analysis is possible when nickel is etched with etchant of the 1:1 mixture of 5% HF:6% $H_2O_2$, and extracted once from an area. Moreover, as explained in association with FIG. 2E, a concentration per a unit of area of the nickel can be obtained. The concentration per a unit of area of nickel can be used to determine the thickness of the nickel since the size of nickel atoms is known. In this example, the thickness of the nickel at the first extraction is approx. 1.338 Å. The foregoing ED-XRF analysis may have an error. Therefore, the nickel layer deposited should be analyzed by a method of multiple samples to reduce the probability of error for determining the thickness.

Figure 6A:
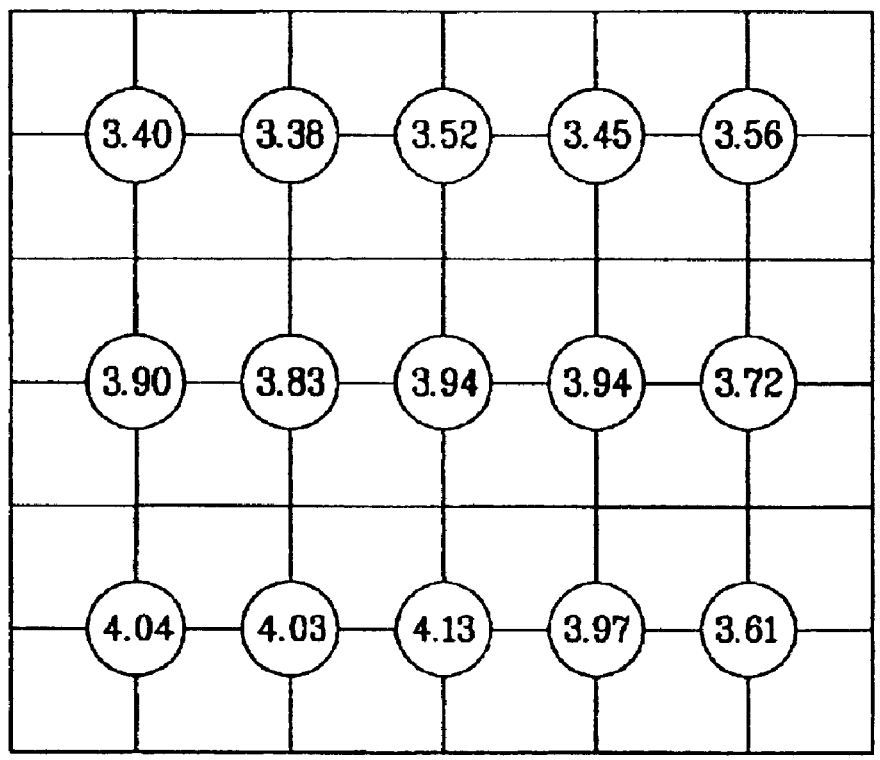
FIGS. 6A to 6C illustrate data of a distributive quantitative analysis of nickel under different sputtering power conditions in depositing nickel by sputtering according to a method for making a quantitative analysis of nickel in accordance with a preferred embodiment of the present invention.
Figure 6B:
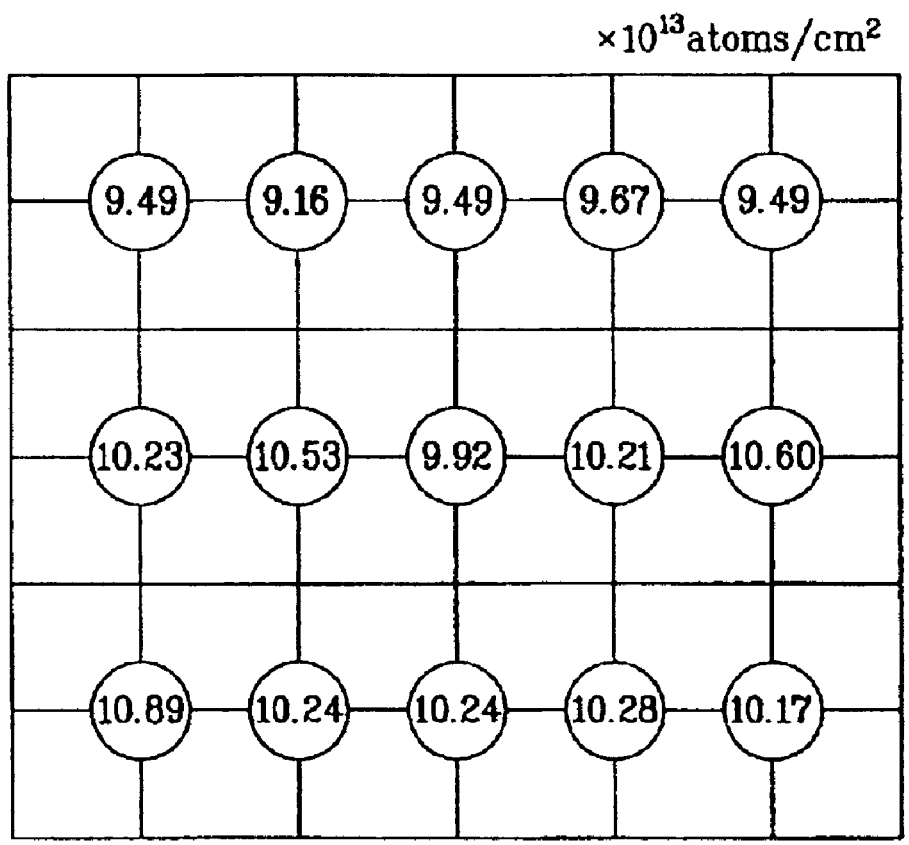
Figure 6C:
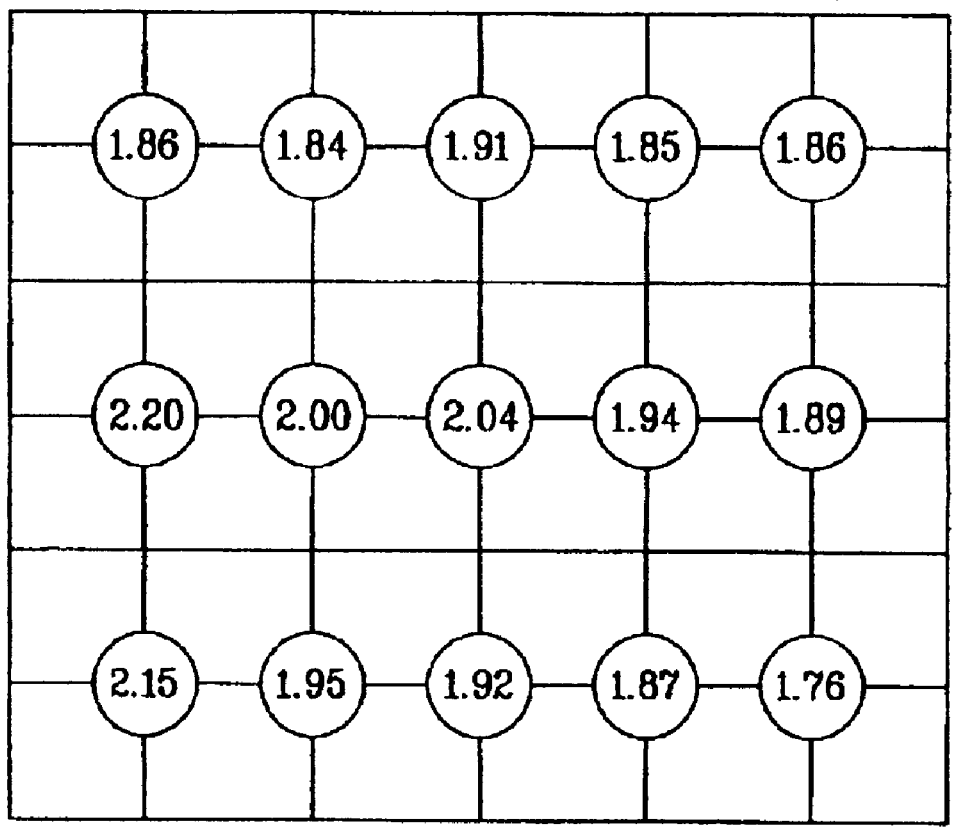

FIGS. 6A to 6C illustrate examples of distributive quantitative data analysis of nickel deposited under different sputtering power conditions according to a method for making a quantitative analysis of nickel in accordance with a first preferred embodiment of the present invention. By taking specimens from across the substrate, distributive quantitative data for the nickel concentrations and/or thickness across the substrate can be determined. FIG. 6A illustrates distributive quantitative data of a concentration of nickel atoms per a unit of area obtained by progressing through the steps described in reference to FIGS. 2A to 2E at different sites across the substrate and subjecting a specimen to ED-XRF analysis from nickel that is sputtered at 100W in Helium gas at a flow rate of 350 sccm. As shown in FIG. 6A, the concentration of nickel ranges from approximately $3.4 \times 10^{13}$ atoms/cm$^2$ to about $4.13 \times 10^{13}$ atoms/cm$^2$ across the substrate. FIG. 6B illustrates distributive quantitative data of a concentration of nickel atoms per a unit of area obtained by progressing through the steps described in reference to FIGS. 2A to 2E at different sites across the substrate and subjecting a specimen to ED-XRF analysis from nickel that is sputtered at 150W in Helium at a flow rate of 350 sccm. As shown in FIG. 6B, the concentration of nickel ranges from approximately $9.16 \times 10^{13}$ atoms/cm$^2$ to about $10.89 \times 10^{13}$ atoms/cm$^2$ across the substrate. FIG. 6C illustrates distributive quantitative data of nickel atoms concentration per a unit of area obtained by progressing through the steps described in reference to FIGS. 2A to 2E at different sites across the substrate and subjecting a specimen to ED-XRF analysis from nickel that is sputtered at 250W at a flow rate of 350 sccm. As shown in FIG. 6C, the concentration of nickel ranges from approximately $1.76 \times 10^{14}$ atoms/cm$^2$ to about $2.20 \times 10^{14}$ atoms/cm$^2$.

As can be noted from the concentrations of nickel in FIGS. 6A to 6C, as the sputtering power increases, the concentration of the nickel atoms in a specimen increases. Therefore, control of the sputtering power is required to control the thickness or concentration of nickel atoms across the surface of the substrate.

Figure 7:
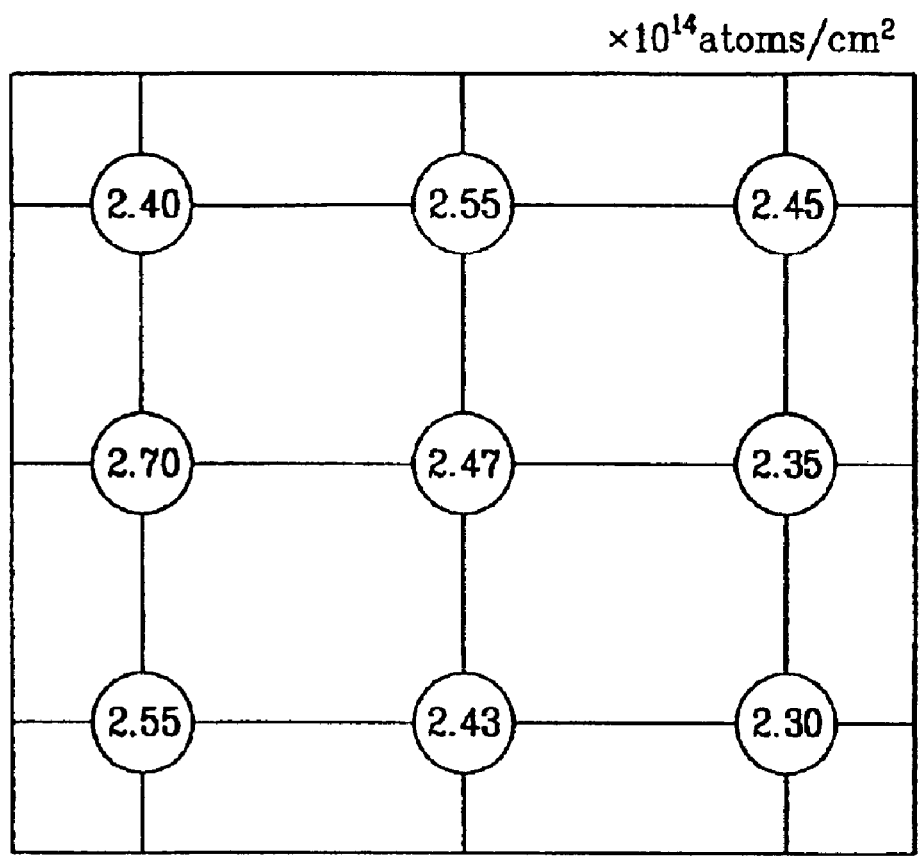
FIG. 7 illustrates distributive quantitative data analysis of nickel in accordance with a preferred embodiment of the present invention.

FIG. 7 illustrates an example of distributive quantitative data analysis of nickel in accordance with a preferred embodiment of the present invention, showing concentration data of nickel atoms per a unit of area across a substrate obtained by the steps described in reference to FIGS. 3A and 3B, and subjecting a specimen to ED-XRF analysis from nickel that is sputtered at 250W and 350 sccm of helium gas. Approximately $2.30 \sim 2.70 \times 10^{14}$ atoms/cm$^2$ is obtained. FIG. 7 compared to FIG. 6C shows that the concentration of nickel atoms per a unit of area is greater in FIG. 7 than in FIG. 6C. This is due to the quantitative analysis data of nickel in FIG. 7 is for nickel deposited on AP1 rather than on an amorphous silicon film. Although the example of the second embodiment of the invention described referring to FIG. 7 has the advantages of the analysis being done within a short time and is simple in comparison to the example of the first embodiment of the invention described referring to FIG. 6C, the first embodiment of the invention is more accurate for making a quantitative analysis of nickel on amorphous silicon.

Figures 8, 9:
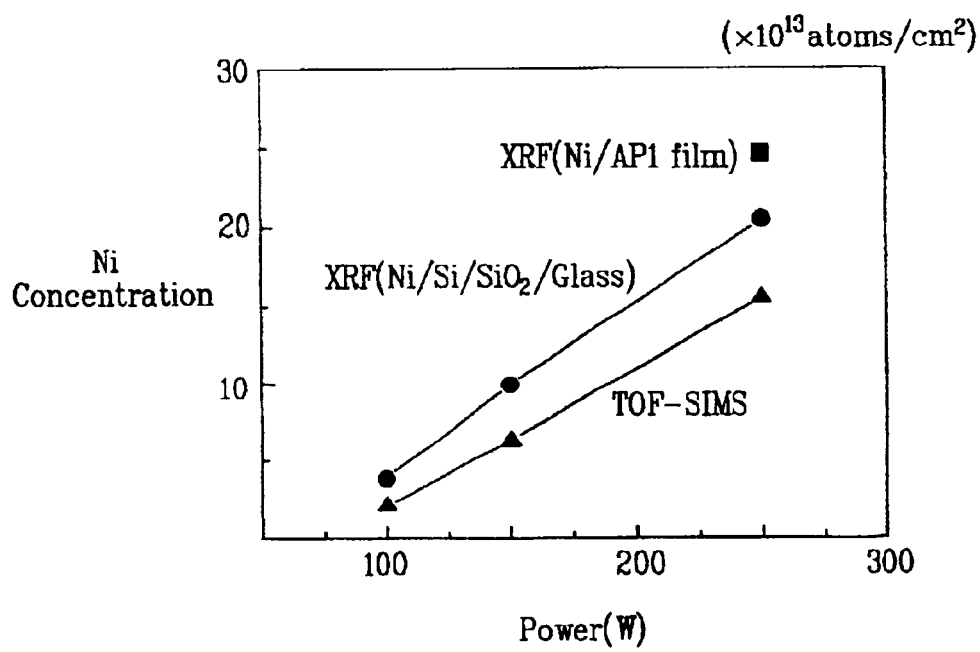
FIG. 8 illustrates a table showing comparison of Energy Dispersive X-ray Fluorescence and TOF-SIMS with respect to the first, and second embodiments of the present invention, and power conditions of nickel sputtering.
FIG. 9 illustrates a graph obtained by plotting the data of FIG. 8.

FIG. 8 illustrates a table showing comparison of ED-XRF and TOF-SIMS with respect to the first and second embodiments of the present invention, and power conditions of nickel sputtering, and FIG. 9 illustrates a graph obtained by plotting the data of FIG. 8. As shown in FIGS. 8 and 9, the concentration of nickel atoms per unit of area increases as the sputtering power increases. FIGS. 8 and 9 also show that the first embodiment using an etchant can analyze a smaller quantity of nickel than the second embodiment using AP1 with nickel deposited directly thereon.

Figure 10A:
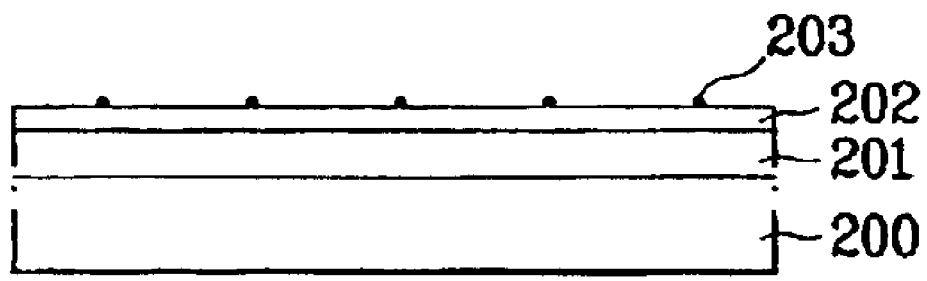
FIGS. 10A and 10B illustrate sections showing the steps of a method for crystallizing amorphous silicon in accordance with a preferred embodiment of the present invention.
Figure 10B:
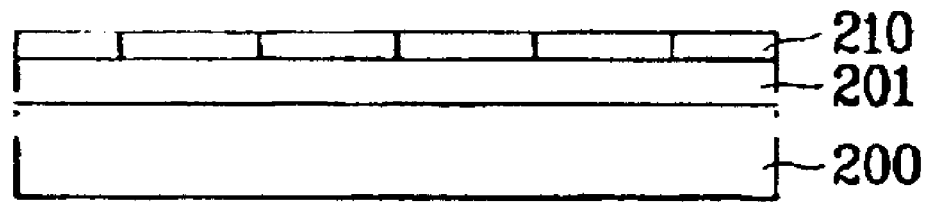

FIGS. 10A and 10B illustrate cross-sections for showing the steps of a method to crystallize amorphous silicon in accordance with a preferred embodiment of the present invention. Referring to FIG. 10A, an insulating film 201, such as $SiO_2$, is deposited on a substrate 200. An amorphous silicon 202 is deposited on the insulating film 201. The insulating film 201 serves as a buffer layer for preventing impurity ions from infiltrating into the amorphous silicon from the substrate 200. A nickel layer 203 is sputtered onto the amorphous silicon 202. The nickel layer 203 is deposited under an optimal condition determined from previous quantitative analysis of nickel in accordance with the present invention.

Referring to FIG. 10B, a heat treatment is conducted at 500~600° C. for approximately four hours, or at 200~500° C. for one hour, with an electric field applied to the nickel and amorphous silicon, to crystallize the amorphous silicon 202 into polycrystalline silicon 210. Complete crystallization of the amorphous silicon can be done and the crystallization temperature of the amorphous silicon can be reduced when the nickel layer 203 is present. When an electric field is applied to the nickel layer 203 and the amorphous silicon layer 202, the crystallization temperature of the amorphous silicon can be further reduced, and a time period required for the crystallization is shortened. The crystallizing method under the presence of the nickel layer 203 is called as Metal Induced Crystallization (MIC), and a method of applying the electric field while using the nickel layer for providing a more favorable condition of the crystallization is called Field Enhanced Metal Induced Crystallization (FEMIC). The nickel layer is deposited to a thickness of less than 1 Å and controlled by controlling the sputtering power as determined by the quantitative analyses of nickel depositions in accordance with the first, or second preferred embodiment of the present invention.

As has been explained, the method for making a quantitative analysis of nickel according to the first embodiment of the present invention has the following advantages. First, the method of analysis is simple, since nickel deposited on a particular region is etched by using an etchant, and subjected to ED-XRF analysis by using AP1 film. Second, cost of the analysis is low, since deposited nickel is etched by using an etchant, and subjected to ED-XRF analysis by using AP1 film. Third, an accurate analysis of a minute amount can be made since the deposited nickel is etched by an etchant that minimizes the size and number of background peaks. The second embodiment described in reference to FIGS. 3A and 3B may alternatively be used if the accuracy of the analysis is not critical or a more simplistic analysis is desired.

It will be apparent to those skilled in the art that various modifications and variations can be made in the method for making quantitative analysis of nickel of the present invention without departing from the spirit or scope of the invention. Thus, it is intended that the present invention cover the modifications and variations of this invention provided they come within the scope of the appended claims and their equivalents.

What is claimed is:

1. A method for making a quantitative analysis of nickel, comprising the steps of:
    providing an amorphous silicon layer;
    forming an insulating film on the amorphous silicon layer;
    depositing nickel on the insulating film;
    etching a defined portion of the nickel with an etchant to create a specimen;
    drying the specimen on an AP1 film; and
    subjecting the dried specimen to energy dispersive X-ray fluorescence analysis.

2. The method as claimed in claim 1, wherein the etchant is a mixture of HF and $H_2O_2$.

3. The method as claimed in claim 2, wherein the mixture of HF and $H_2O_2$ is 5% HF and 6% $H_2O_2$ mixed in a 1:1 ratio.

4. The method as claimed in claim 1, wherein the drying the specimen on an AP1 film includes placing the AP1 film with the specimen on a hot plate.

5. The method as claimed in claim 1, wherein the step of etching a defined portion of the nickel with an etchant to create a specimen includes the steps of:
    forming a donut of photoresist on the nickel layer;
    dropping the etchant within the inside of the donut of photoresist; and
    extracting the specimen from inside of the donut of photoresist.

6. The method as claimed in claim 1, further comprising:
    measuring a value of a nickel peak from the energy dispersive X-ray fluorescence analysis; and
    determining a concentration per a unit of area based upon the value of the nickel peak together with an area of the defined portion.

7. A method for making quantitative analysis of nickel, comprising the steps of:
    providing a substrate;
    placing an AP1 film having a predetermined area on the substrate;
    depositing nickel on the AP1 film;
    peeling the AP1 off of the substrate; and
    subjecting the peeled AP1 film to energy dispersive X-ray fluorescence analysis.

8. The method as claimed in claim 7, wherein the step of depositing nickel on the AP1 film includes sputtering the nickel on the AP1 film.

9. The method as claimed in claim 7, further comprising:
    measuring a value of a nickel peak from the energy dispersive X-ray fluorescence analysis; and
    determining a concentration per a unit of area based upon the value of the nickel peak together with the predetermine area.

10. A method for crystallizing amorphous silicon comprising the steps of:
    depositing nickel under different depositing conditions;
    etching a predetermined area of nickel in each deposition with etchant to prepare specimens for each of the depositing conditions;
    drying the specimens on AP1 film;
    subjecting the specimens to energy dispersive X-ray fluorescence analysis;
    determining an optimal nickel depositing condition according to results of the energy dispersive X-ray fluorescence analyses on the specimens;
    depositing nickel on amorphous silicon with the optimal depositing condition; and
    crystallizing the amorphous silicon into polycrystalline silicon.

11. A method as claimed in claim 10, wherein the etchant is 5% HF and 6% $H_2O_2$ mixed in a 1:1 ratio.

12. The method as claimed in claim 10, wherein drying the specimens on AP1 film includes placing the AP1 film with the specimen on a hot plate.

13. The method as claimed in claim 10, wherein the step of etching a predetermined area of nickel in each deposition with etchant to prepare specimens for each of the depositing conditions includes the steps of:
    forming a donut of photoresist on the nickel layer for each of the depositing conditions;
    dropping etchant within the inside of the donuts of photoresist; and
    extracting the specimens from inside of the donuts of photoresist.

14. The method as claimed in claim 10, wherein the step of depositing nickel under different depositing conditions includes nickel sputtering.

15. The method as claimed in claim 10, wherein the step of crystallizing the amorphous silicon includes using the metal induced crystallization method.

16. The method as claimed in claim 10, wherein the step of crystallizing the amorphous silicon includes using the field enhanced metal induced crystallization method.

17. A method for crystallizing amorphous silicon comprising the steps of:
    providing substrates;
    placing an AP1 film having a predetermined area on each of the substrates;
    depositing nickel on the AP1 film on each substrate such that there are depositions of nickel under different depositing conditions;
    peeling the AP1 film off of the substrates;
    subjecting the nickel deposited AP1 film to energy dispersive X-ray fluorescence analysis;

determining an optimal nickel depositing condition according to results of the energy dispersive X-ray fluorescence analyses on the specimens;

depositing nickel on amorphous silicon with the optimal depositing condition; and crystallizing the amorphous silicon into polycrystalline silicon.

18. The method as claimed in claim 17, wherein the step of depositing nickel on the AP1 film on each substrate such that there are depositions of nickel under different depositing conditions includes nickel sputtering.

19. The method as claimed in claim 17, wherein the step of crystallizing the amorphous silicon into polycrystalline silicon includes using the metal induced crystallization method.

20. The method as claimed in claim 17, wherein the step of crystallizing the amorphous silicon into polycrystalline silicon includes using the field enhanced metal induced crystallization method.

* * * * *